(12) United States Patent
Kerr et al.

(10) Patent No.: US 10,467,748 B2
(45) Date of Patent: Nov. 5, 2019

(54) TISSUE SAMPLE ANALYSIS TECHNIQUE

(71) Applicant: Oxford Cancer Biomarkers Ltd, Oxford (GB)

(72) Inventors: David Kerr, Oxford (GB); John Maddison, Crowborough (GB); Havard Danielsen, Oslo (NO)

(73) Assignee: Oxford Cancer Biomarkers Ltd, Oxford (GB)

( * ) Notice: Subject to any disclaimer, the term of this patent is extended or adjusted under 35 U.S.C. 154(b) by 0 days.

(21) Appl. No.: 15/559,183

(22) PCT Filed: Mar. 10, 2016

(86) PCT No.: PCT/EP2016/055102
§ 371 (c)(1),
(2) Date: Sep. 18, 2017

(87) PCT Pub. No.: WO2016/146469
PCT Pub. Date: Sep. 22, 2016

(65) Prior Publication Data
US 2018/0075598 A1 Mar. 15, 2018

(30) Foreign Application Priority Data
Mar. 18, 2015 (GB) .................................. 1504569.3

(51) Int. Cl.
*G06T 7/00* (2017.01)
*A61B 10/02* (2006.01)
*G06K 9/46* (2006.01)
*G06K 9/62* (2006.01)

(52) U.S. Cl.
CPC ........ *G06T 7/0012* (2013.01); *A61B 10/0241* (2013.01); *G06K 9/4652* (2013.01); *G06K 9/6223* (2013.01); *G06K 9/6267* (2013.01); *G06K 2209/05* (2013.01); *G06T 2207/10056* (2013.01); *G06T 2207/30024* (2013.01)

(58) Field of Classification Search
None
See application file for complete search history.

(56) References Cited

U.S. PATENT DOCUMENTS 9,076,198 B2 * 7/2015 Yoshihara ............. G06T 7/0012
9,230,063 B2 * 1/2016 Bhargava ............. G06F 19/345
9,779,283 B2 * 10/2017 Bhargava ............. G06K 9/6228
(Continued)

OTHER PUBLICATIONS

A. Huijbers et al: "The proportion of tumor-stroma as a strong prognosticator for stage II and III colon cancer patients: validation in the VICTOR trial", Annals of Oncology., vol. 24, No. 1, Aug. 2, 2012 (Aug. 2, 2012), pp. 179-185, XP055271228, NL ISSN: 0923-7534, DOI: 10.1093/annonc/mds246 the whole document.
(Continued)

*Primary Examiner* — Nancy Bitar
(74) *Attorney, Agent, or Firm* — Leason Ellis LLP

(57) ABSTRACT

Quantitative analysis of a tissue sample includes carrying out a ploidy measurement on a plurality of nuclei of the sample to determine the ploidy type of a sample and also carrying out a stroma measurement on a section to determine the stroma type of a sample. The ploidy type, e.g. diploid or non-diploid, and the stroma type, high or low stroma, give an improved patient survival estimate than the ploidy type alone.

11 Claims, 14 Drawing Sheets

(56) References Cited

U.S. PATENT DOCUMENTS

| | | | |
|---|---|---|---|
| 10,055,551 B2* | 8/2018 | Agaian | G06N 3/0427 |
| 10,192,099 B2* | 1/2019 | Agaian | G16H 50/30 |
| 2010/0088264 A1* | 4/2010 | Teverovskiy | G16H 50/20 706/46 |
| 2018/0293427 A1* | 10/2018 | Syvertsen | G06K 9/00147 |

OTHER PUBLICATIONS

Ehteshami Bejnordi Babak et al: "Quantitative analysis of stain variability in histology slides and an algorithm for standardization", Progress in Biomedical Optics and Imaging, SPIE—International Society for Optical Engineering, Bellingham, WA, US, vol. 9041, Mar. 20, 2014 (Mar. 20, 2014), pp. 904108-904108, XP060030747, ISSN: 1605-7422, DOI: 10.1117/12.2043683 ISBN: 978-1-5106-0027-0 the whole document.

Tabesh A et al: "Multifeature Prostate Cancer Diagnosis and Gleason Grading of Histological Images", IEEE Transactions on Medical Imaging, IEEE Service Center, Piscataway, NJ, US, vol. 26, No. 10, Oct. 1, 2007 (Oct. 1, 2007), pp. 1366-1378, XP01119321, ISSN: 0278-0062, DOI: 10.1109/TMI.2007.898536 p. 1368, right-hand column, paragraph 1-paragraph 2.

Agarwal Nitin et al: "DNA ploidy measure of Feulgen-stained cancer cells using three-dimensional image cytometry", 2014 IEEE Healthcare Innovation Conference (HIC), IEEE, Oct. 8, 2014 (Oct. 8, 2014), pp. 6-9, XP032734965, DOI: 10.1109/HIC.2014.7038861 [retrieved on Feb. 10, 2015] First sentence of abstract.

Rosario Carrillo et al: "Prognostic Significance of DNA Ploidy and Proliferative Index (MIB-1 Index) in Gastrointestinal Stromal Tumors", Human Pathology, Feb. 1, 1997 (Feb. 1, 1997), pp. 160-165, XP055271295, DOI: 10.1016/S0046-8177(97)90100-3 Retrieved from the Internet: URL:http://ac.els-cdn.com/S0046817797901003/1-s2.0-S0046817797901003-main.pdf?_tid=570a03f8-15fa-11e6-8747-00000aab0f6c&acdnat=14628077429e53d2a02d2e88a3b68bda49a0667bab [retrieved on May 9, 2016] Title.

T. J. A. Dekker et al: "Prognostic significance of the tumor-stroma ratio: validation study in node-negative premenopausal breast cancer patients from the EORTC perioperative chemotherapy (POP) trial (10854)", Breast Cancer Research and Treatment., vol. 139, No. 2, May 25, 2013 (May 25, 2013), pp. 371-379, XP055271370, US ISSN: 0167-6806, DOI: 10.1007/s10549-013-2571-5 the whole document.

* cited by examiner

TISSUE SAMPLE ANALYSIS TECHNIQUE

CROSS-REFERENCE TO RELATED APPLICATIONS

The present application is a U.S. National Phase Application under 35 U.S.C. § 371 of International Patent Application No. PCT/EP2016/055102, filed Mar. 10, 2016, which claims priority of Great Britain Application Serial No. 1504569.3, filed Mar. 18, 2015, each of which is hereby incorporated by reference as if expressly set forth in their respective entirety herein. The International Application was published in English on Sep. 22, 2016 as WO 2016/146469.

BACKGROUND TO THE INVENTION

In many cancer types it is at the time of diagnosis difficult for the clinician to predict the tumour's growth and behaviour. The predictions made at this time affect the type of treatment for the patient and can therefore have large consequences for the future outcome and his or her life quality. Cancer treatment can be a hard stress, and if the patient's tumour is indolent, an aggressive treatment might actually cause more pain and discomfort than the cancer itself. To separate the aggressive tumours from the indolent ones at the time of diagnosis, and further to choose the right treatment, is a main challenge in cancer care.

Digital image analysis of cell nuclei and other structures is a useful method to obtain quantitative information from tissue. Methods can be employed that complete analysis of both isolated cell nuclei and that of the surrounding tissue. As such there is motivation to develop automatic systems that can capture these cell nuclei from the original medium, gather a significant population of nuclei and characterise them.

It can be appreciated that methods allowing the characterisation of cell nuclei have drug discovery, clinical and other medical applications.

SUMMARY OF THE INVENTION

According to the invention there is provided a method of quantitative analysis of a tissue sample, comprising:
  carrying out a ploidy measurement on a pluality of nuclei of the sample to determine the ploidy type of the sample;
  carrying out a stroma measurement on a section of the tissue sample to determine the stroma type of a sample by determining whether the sample is a high stroma type having a percentage of stroma above a predetermined stroma percentage or a low stroma type having a percentage of stroma at most the predetermined stroma percentage;
  and outputting a classification based on the stroma type and the ploidy type.

The classification may be a classification such as "high", "intermediate" of "low" risk or alternatively the classification may simply be a combination of the stroma type and ploidy type, for example "diploid, low stroma". Either way, a better prognosis can be obtained than could be expected than by using ploidy type alone.

The ploidy measurement may be carried out by
  preparing a sample of the tissue such that nuclei are liberated and stained with a DNA specific stain;
  capturing a microscope image of the nuclei specimen, segmenting the image in the captured image to identify the nuclei;
  for each of a plurality of nuclei, obtaining the integrated optical density; and
  determining the DNA ploidy classification for the sample.

The stroma measurement may be carried out by:
  obtaining a tissue section;
  staining the tissue section;
  capturing a microscope image of the stained tissue section;
  using a clustering algorithm to segment the image pixels of the microscope image into stroma and non-stroma pixels; and
  calculating the fraction of stroma pixels in the image; and determining whether the fraction of stroma pixels exceeds the predetermined stroma percentage.

The step method may further include converting the captured microscope image to hue-saturation-value colour coordinates before carrying out the step of using a clustering algorithm.

The step of using a clustering algorithm may include fitting the image pixels to two Gaussian curves, one Gaussian curve corresponding to stroma and one corresponding to non-stroma regions of the image.

In one approach, the method of obtaining a stroma fraction includes:
  converting the captured image into a normalised Haemotoxylin image representing the areas of the image stained with Haemotoxlyin and a normalised Haemotoxylin and eosin image representing the areas of the image stained with either Haemotoxylin or eosin;
  calculating a background mask of pixels in the normalised Haemotoxylin and eosin image having saturation below a first predetermined level and value below a second predetermined level corresponding to the background of the image; and
  calculating a connective tissue mask by converting the normalised Haemotoxyin image to gray to obtain a gray-converted image, wherein the step of using a clustering algorithm uses a clustering algorithm and thresholding on the gray converted image to identify pixels of connective tissue.

The predetermined stroma percentage may be 30% to 70%, for example 40% to 60%.

The method may also include calculating a patient survival group from the stroma type and the ploidy type.

A sample of stroma type high stroma and a ploidy type of non-diploid may be indicated as high risk, a sample of stroma type low stroma and ploidy type diploid may be indicated as low risk, and wherein samples having a stroma type of low stroma and a ploidy type of non-diploid type or a stroma type of high stroma and a ploidy type of diploid may be indicated as at an intermediate level of risk.

The analysis that is performed by the present invention allows for characterisation of samples by combining the combination of quantitative evaluation of nuclei population and the quantity of stromal tissue within a tissue section, where a tissue section, typically obtained from a biopsy contains many different types of tissue, epithelial, stroma, muscle, lumen and mucinous area and others.

The present invention allows for quantitative information to be obtained by combining quantitative information obtained on individual isolated cell nuclei and quantitative information from tissue sections.

The sample may be of cancerous tissue. In particular examples, the cancerous tissue may be colon tissue, rectal tissue or prostate tissue.

In another aspect, the invention relates to a computer program product arranged to cause a computer to carry out a method as set out above.

In another aspect, the invention relates to a method of measuring the percentage of stroma in a tissue by:
  obtaining a tissue section;
  staining the tissue section;
  capturing a microscope image of the stained tissue section;
  converting the captured microscope image to hue-saturation-value colour coordinates;
  fitting the hue value of the image pixels to two Gaussian curves, one Gaussian curve corresponding to stroma and one corresponding to non-stroma regions of the image to segment the image pixels of the microscope image into stroma and non-stroma pixels; and
  calculating the fraction of stroma pixels in the image.

In this way, the percentage of stroma may reliably be obtained automatically without requiring a physician.

The method may further comprising determining whether the sample is a high stroma type having a percentage of stroma above a predetermined stroma percentage or a low stroma type having a percentage of stroma at most the predetermined stroma percentage.

A further aspect relates to a method of measuring the percentage of stroma in a tissue from a captured microscope image of a stained tissue section by:
  converting the captured image into a normalised Haemotoxylin image representing the areas of the image stained with Haemotoxlyin and a normalised Haemotoxylin and eosin image representing the areas of the image stained with either Haemotoxylin or eosin;
  calculating a background mask of pixels in the normalised Haemotoxylin and eosin image having saturation below a first predetermined level and value below a second predetermined level corresponding to the background of the image;
  converting the normalised Haemotoxyin image to gray to obtain a gray-converted image;
  using a clustering algorithm and thresholding on the gray converted image to obtain a connective tissue mask identifying pixels of connective tissue; and
  obtaining the percentage of stroma from the percentage of connective tissue identified by the connective tissue mask in the image excluding background identified by the background mask.

BRIEF DESCRIPTION OF THE DRAWINGS

For a better understanding of the invention, embodiments will now be described, purely by way of example, with reference to the accompanying drawings, in which.

DESCRIPTION

In an embodiment, tissue samples previously removed from a cancerous region for biopsy is used to prepare a tissue section used for a stroma measurement and further cells from the sample are used for a ploidy measurement. These are discussed in more detail below.

Ploidy Measurement

Figure 1:
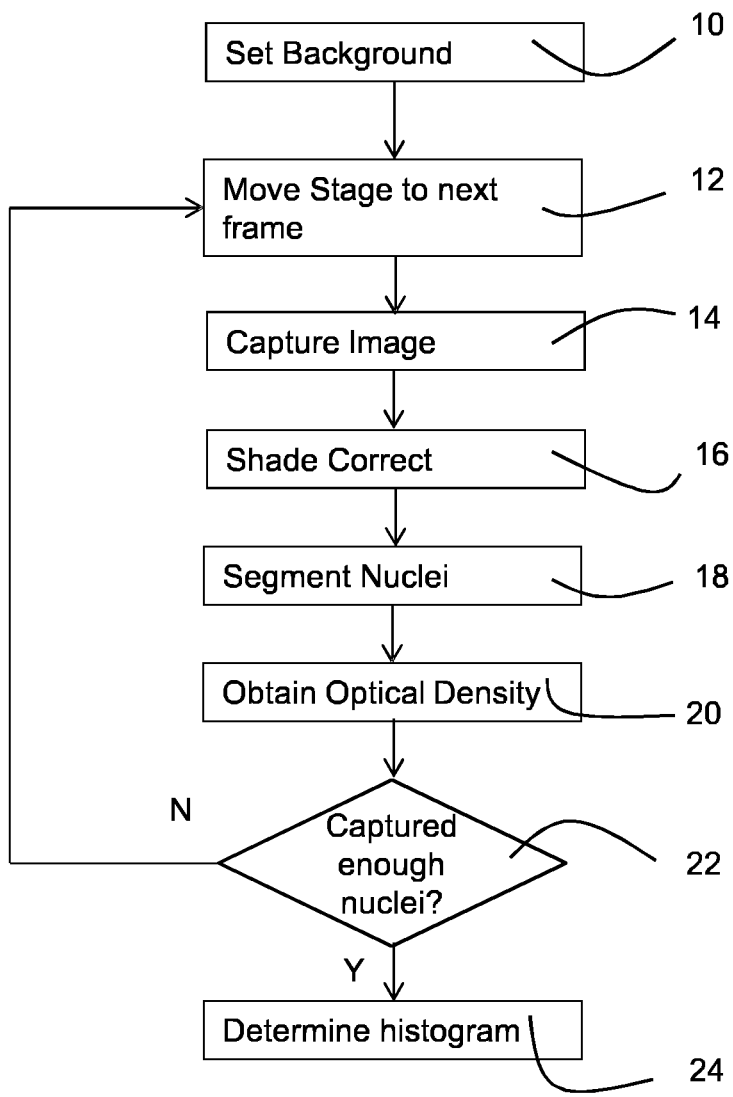
FIG. 1 shows a flow diagram illustrating carrying out a ploidy measurement.
Figure 2:
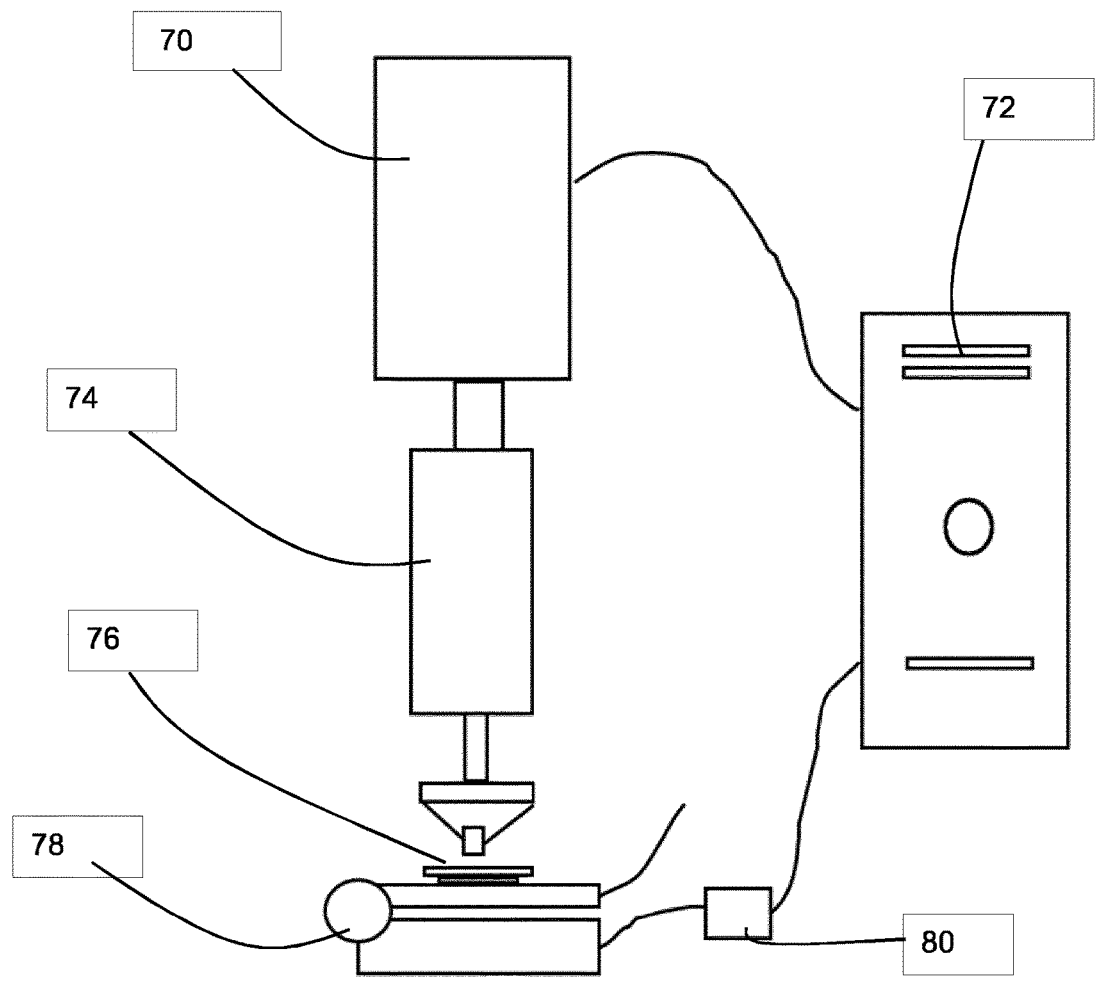
FIG. 2 shows apparatus for carrying out the ploidy measurement of FIG. 1.

Referring to FIGS. 1 and 2, microscopy equipment and digital image capture equipment is used for the analysis of cell nuclei, specifically the chromatin within the nuclei in order to obtain quantitative information about the chromatin structure within the cell nuclei. The embodiment uses the grey scale intensity data from the prepared nuclei to complete the analysis.

A cell specimen is first prepared from the tissue sample using standard laboratory procedures to make a mono-layer stained layer on slide 76 using the Feulgen method. The method is well known and described for example in Ris and Mirsky, "Quantitative Cytochemical determination of desoxyribonucleic acid with the Feulgen nucleal reaction.", The Journal of General Physiology, (1949) pages 125 to 146 Note that this technique includes a homogenizing or liberating step so the resulting stained sample is of a homogenized set of cells, not a cell section.

The prepared slide 76 is placed onto a microscope 74, in particular onto computer controlled stage 78. The microscope 74 uses an imaging device 70. A personal computer 72 programmed by computer software according to the embodiment controls control electronics 80 which controls the stage 78 to move the stage and the specimen and hence the location of the slide under the microscope. The personal computer 72 drives the stage 78 to the required position and the digital camera is used to capture the image once the specimen is in the required location.

The computer is used to control the digital camera and also to complete the subsequent analysis. The computer carries out the set of steps illustrated in FIG. 1.

Firstly, (step 10) a background level is calculated for the image as a whole, by taking a reference area clear from nuclei and other artifacts.

Next, the stage 78 is moved to a first frame position (step 12), and an image captured (step 14).

The image is then processed by correcting for shade (step 16) and segmenting the nuclei (step 18). Further details of the segmentation algorithm used are provided in GB 1019429.8.

The integrated optical density of each nucleus is then obtained (step 20). If sufficient nuclei have been captured, i.e. if the number of nuclei for which the integrated optical intensity exceeds a predetermined number, then the method proceeds to step 24. However, if an insufficient number of nuclei have been measured, then the method returns to step 12, where the stage is moved to a new location to capture an image of further nuclei. These steps are repeated until either the whole sample has been measured or the number of nuclei exceeds the predetermined number.

Figure 3:
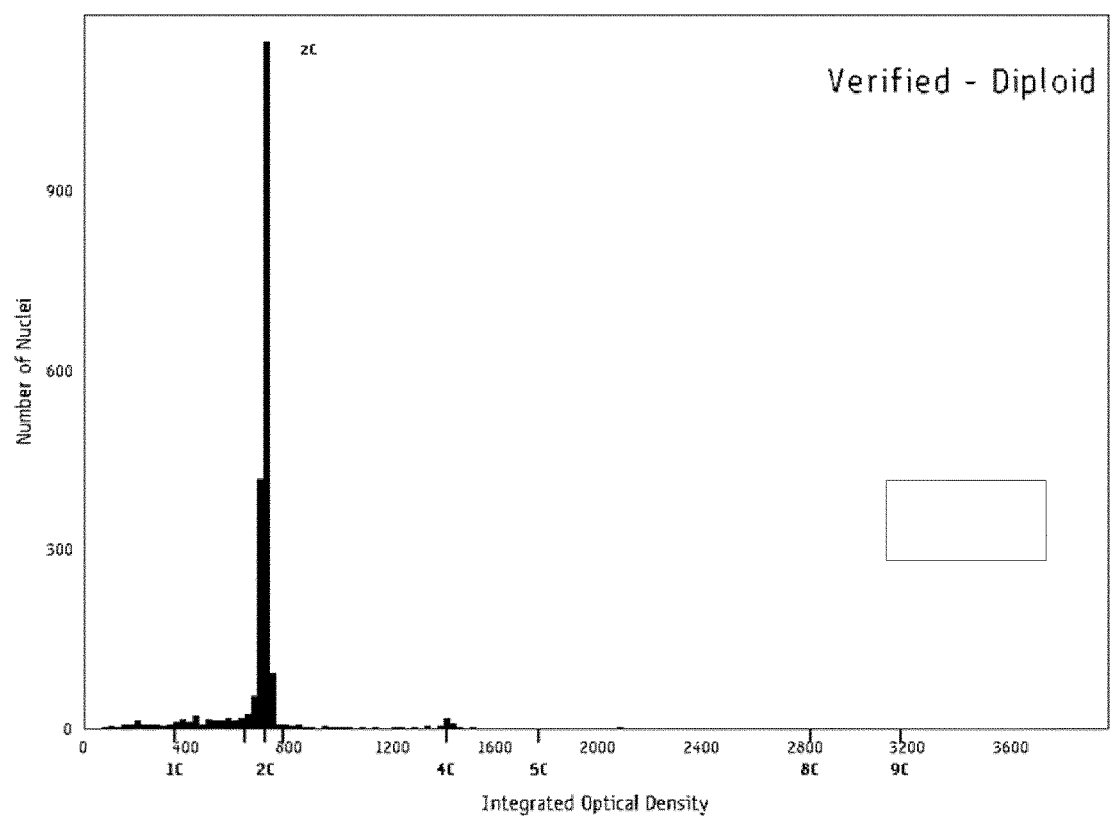
FIG. 3 shows an example ploidy measurement of a normal sample.

A histogram may then be obtained (step 24) to determine the range of integrated optical densities. This is used to determine the DNA ploidy classification whether the sample is a diploid sample with a single large peak at the 2C position as illustrated in FIG. 2 or non-diploid as illustrated in FIG. 3. Note that in practice the histogram need not be calculated or plotted as such—all that is required is that the data from the nuclei is stored and that the personal computer 72 can classify the data as set out below.

Figure 4:
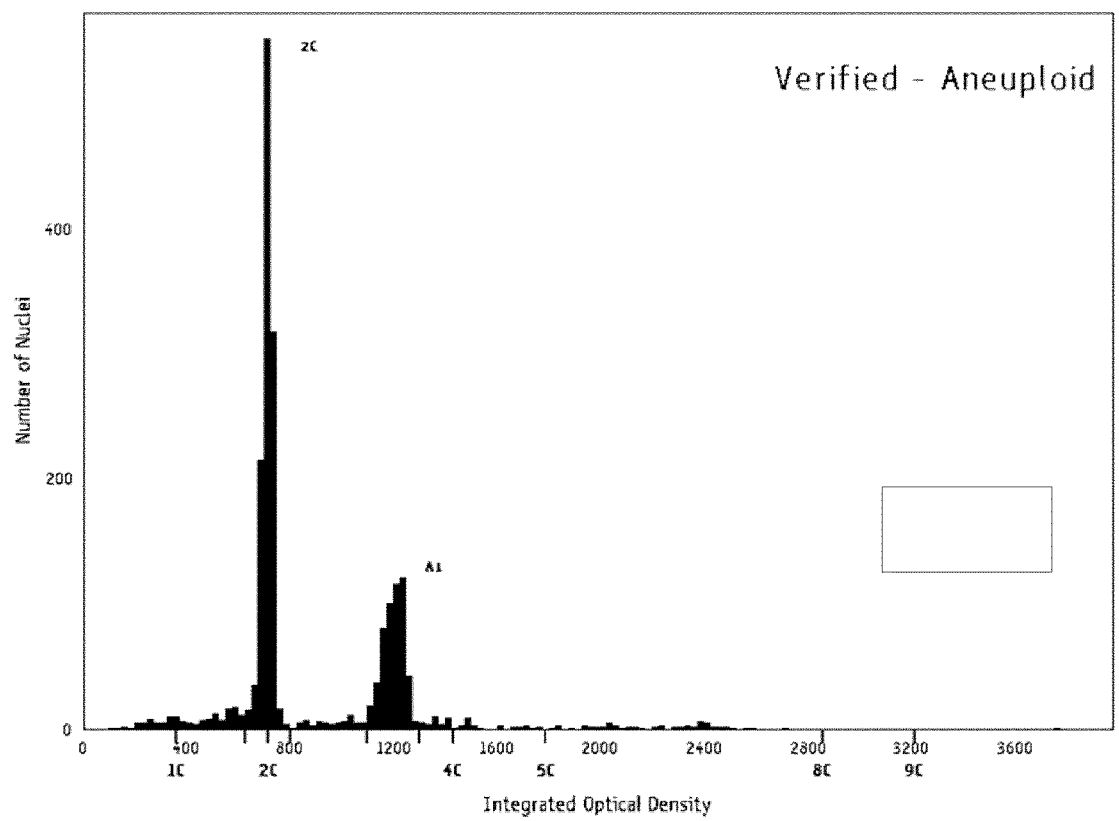
FIG. 4 shows an example ploidy measurement of an abnormal sample.

FIGS. 3 and 4 illustrate histograms from two samples.

FIG. 3 shows a histogram of the number of nuclei with a variety of integrated optical densities, corresponding to the ploidy of the sample. The scale indicates the optical densities corresponding to Haploid number of 1c, 2c, 4c and 5c. These optical densities correspond to the number of copies of chromosomes in the cell. 2c is a diploid cell, and 4c is a cell in the process of division.

FIG. 4 shows a corresponding histogram for an aneuploid sample. In this case, as well as a significant peak at 2c there is also a significant peak at an aneuploid value intermediate between the 2c and 4c peaks. This corresponds to a non-diploid sample.

In the specific example of the classification of DNA ploidy, a tumor was classified as diploid if only one G0/G1 peak (2c) was present, the number of nuclei at the G2 peak (4c) did not exceed 10% of the total number of nuclei and the number of nuclei with DNA content more than 5c did not exceed 1%.

A tumor was defined as tetraploid if a 4c peak (DI 1.9-2.1) was present (the number of nuclei at 4c peak is more than the S-phase fraction and more than 10% of the total nuclei), the number of nuclei at G2 peak (8c) did not exceed 10% of the total number of nuclei and the number of nuclei with DNA content more than 9c did not exceed 1%.

A tumor was defined as polyploid when more than 10% of total number of nuclei was present at 8c peak and/or number of nuclei with DNA content more than 9c exceeded 1%.

A tumor was defined as aneuploid when non euploid peak(s) were present or the number of nuclei with a DNA content exceeding 5c, not representing euploid populations, exceeded 1%. A tumour was classified as hyperdiploid if an aneuploid peak was demonstrated with DNA index 1.06-1.10.

Stroma Measurement

Figure 5:
FIG. 5 illustrates a stroma image after sectioning and staining.

A tissue sample is obtained, sectioned and stained to obtain an image as illustrated in FIG. 5. Hematoxylin and eosin stain is used to prepare the sections.

Figure 6:
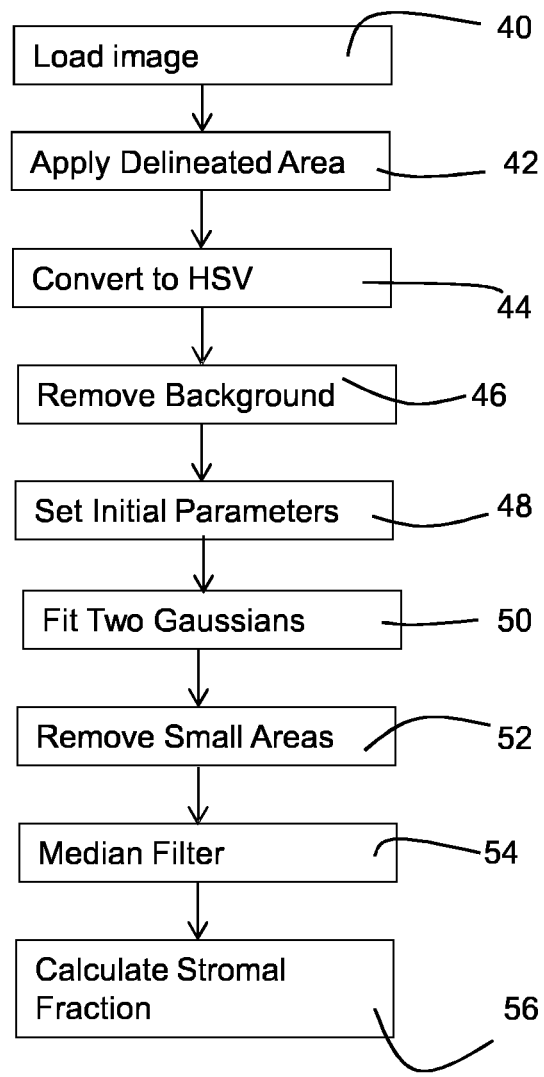
FIG. 6 shows a flow diagram illustrating carrying out a stroma measurement.

Then, referring to FIG. 6, a colour image of the section is captured using a slide scanner (step 40) and uploaded to a computer. The image is then converted to hue-saturation-value colour coordinates (step 42).

Next the background is removed (step 46). This is done by identifying a region of the image with no tissue.

A fit to two Gaussians is then carried out. Initial conditions are set (step 48) and then a clustering algorithm used (step 50) to fit two different colours to the data, each represented by a different Gaussian. This effectively divides the image between stroma and non-stroma. This clustering algorithm uses the hue value only of the colour image.

Next, small areas below a certain number of pixels are removed (step 52), and the image passed through a median filter (step 54) to remove noise in the image.

The stromal fraction is then calculated (step 56). Samples are identified as being high stroma when the stroma fraction is above a predetermined value, for example in the range: 50%, for example. The other samples are classified as low stroma.

Combination

Figure 7:
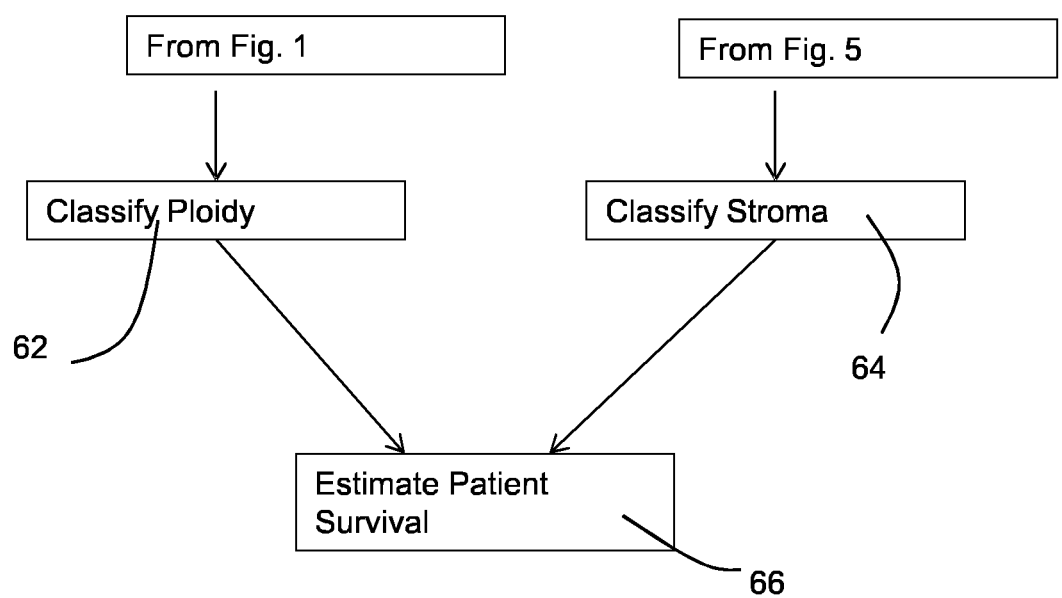
FIG. 7 shows a flow diagram illustrating a combined method.

FIG. 7 illustrates the combined method, starting from a tissue sample.

The histogram resulting from the method illustrated in FIG. 1 is classified as having a ploidy type of either diploid or non-diploid (step 62). In this case, any results that are tetraploid, polyploid or aneuploid are classified as non-diploid. The skilled person will realise that there are other calculations that can classify the sample as diploid or non-diploid without requiring a histogram, and such methods are equally possible.

The stroma fraction resulting from the method illustrated in FIG. 6 is also classified either as high stroma or low stroma (step 64).

Then, the combined classifications are used to calculate expected relapse rate after a particular time. Equivalently, the data may be used to capture the relapse free survival rate. Alternatively, data relating to patient survival may be captured instead. This data can provide useful information to a physician who may choose more aggressive intervention when the life expectancy is otherwise lower.

Estimates of patient relapse rate may be obtained by experiment. The inventors have discovered that a combination of the two methods gives unexpectedly good results.

An experiment was carried out on two patient series, a first series "V" being a series of 850 patients with colorectal cancer stage II or III enrolled in a trial at Oxford and a second series "A" being a series of 587 patients with colorectal cancer stage I, II or III, at Oslo University hospital. All patients have had the tumor surgically removed. Patients with stage III under 75 years have received additional (adjuvant) chemotherapy. All patients have been followed up for at least 5 years or until death.

The samples were classified both on the DNA ploidy method described above as diploid or non-diploid, and also on the stroma measurement described above and classified as either low stroma or high stroma.

The relapse rates were plotted in different ways. The graphs presented are labelled D for diploid or N for non-diploid, H for high stroma and L for low stroma.

Figure 8:
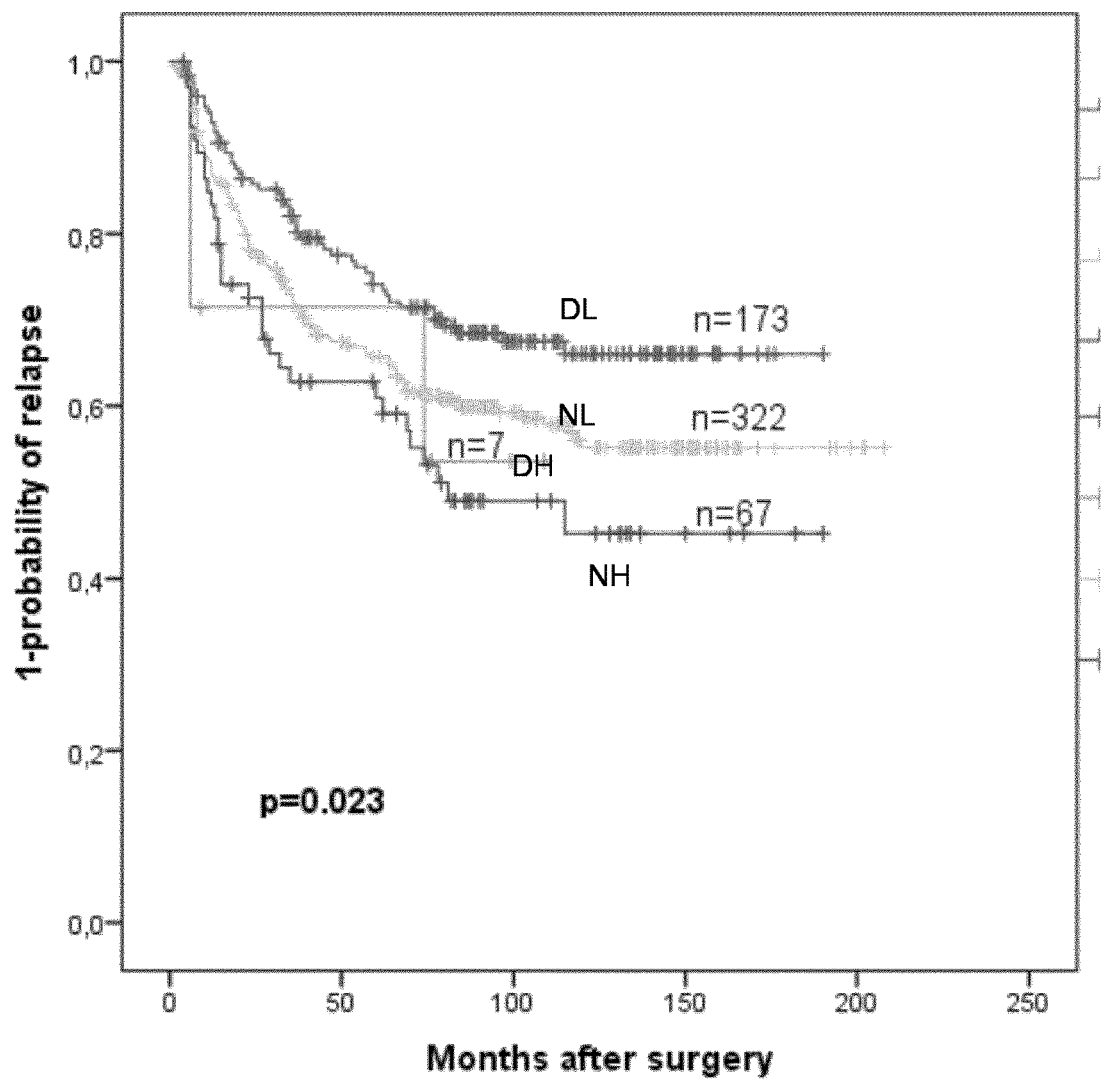
FIG. 8 shows patient survival results in an example using both ploidy and stroma classifications.

FIG. 8 plots the relapse-free survival rates for a number of years after the measurements for the series A.

Note that the combination of measurements using both stroma type and ploidy type gives good separation of the non-diploid high stroma with a 5-year relapse-free survival rate of 50% and the diploid low stroma with a much higher 5-year relapse-free survival rate.

Figure 9:
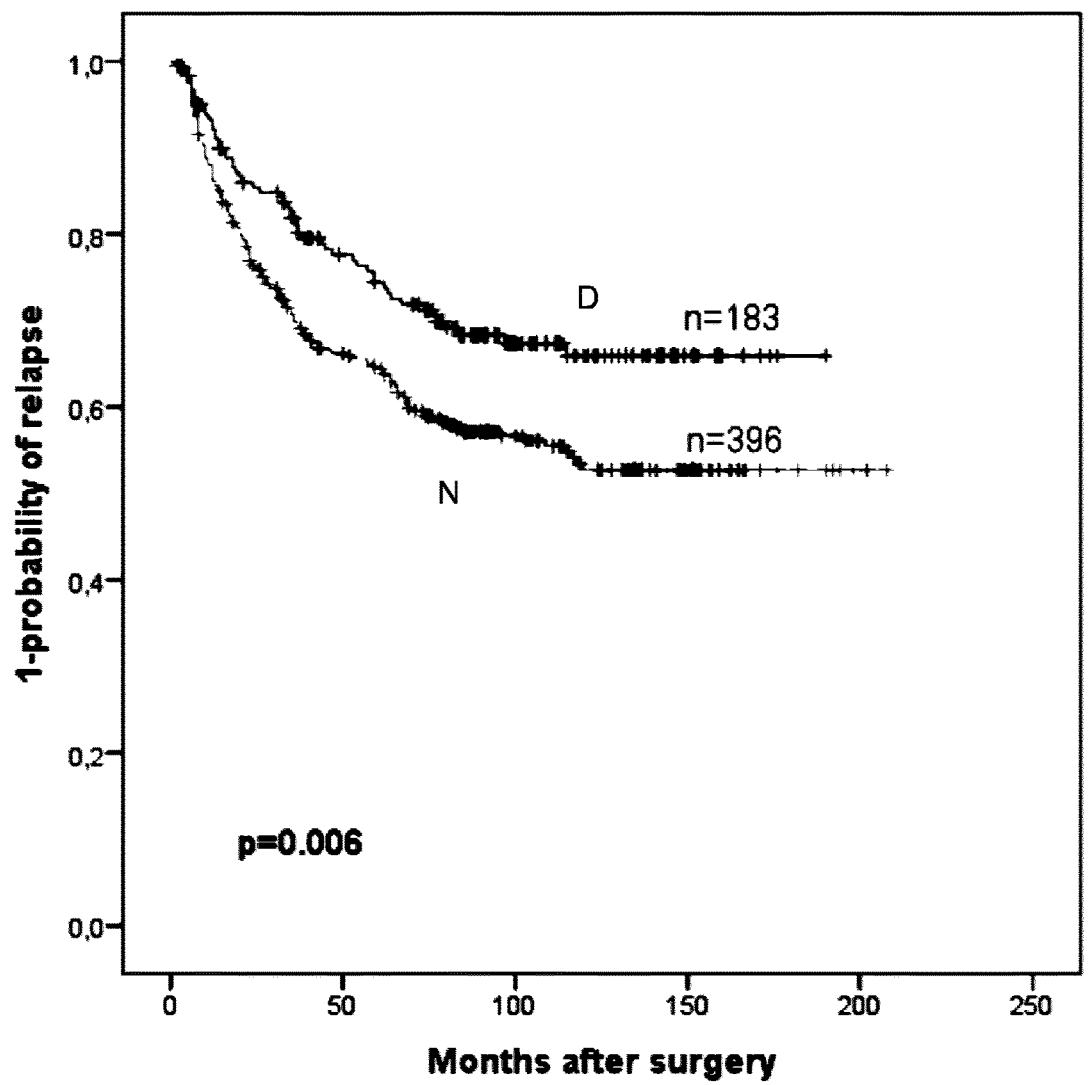
FIG. 9 shows patient survival results using only a ploidy classification.

The separation of these graphs is much better than illustrated in FIG. 9 which shows the results separated only by ploidy type of diploid or non-diploid (ploidy).

Thus, it is apparent that the combination of the two methods gives much better results than simply looking at a classification based on ploidy. Thus, by outputting both the information regarding the diploid type and the stroma type output data is provided that allows a physician to more accurately estimate the prognosis, i.e. relapse free survival rate, and hence select appropriate treatment.

Figure 10:
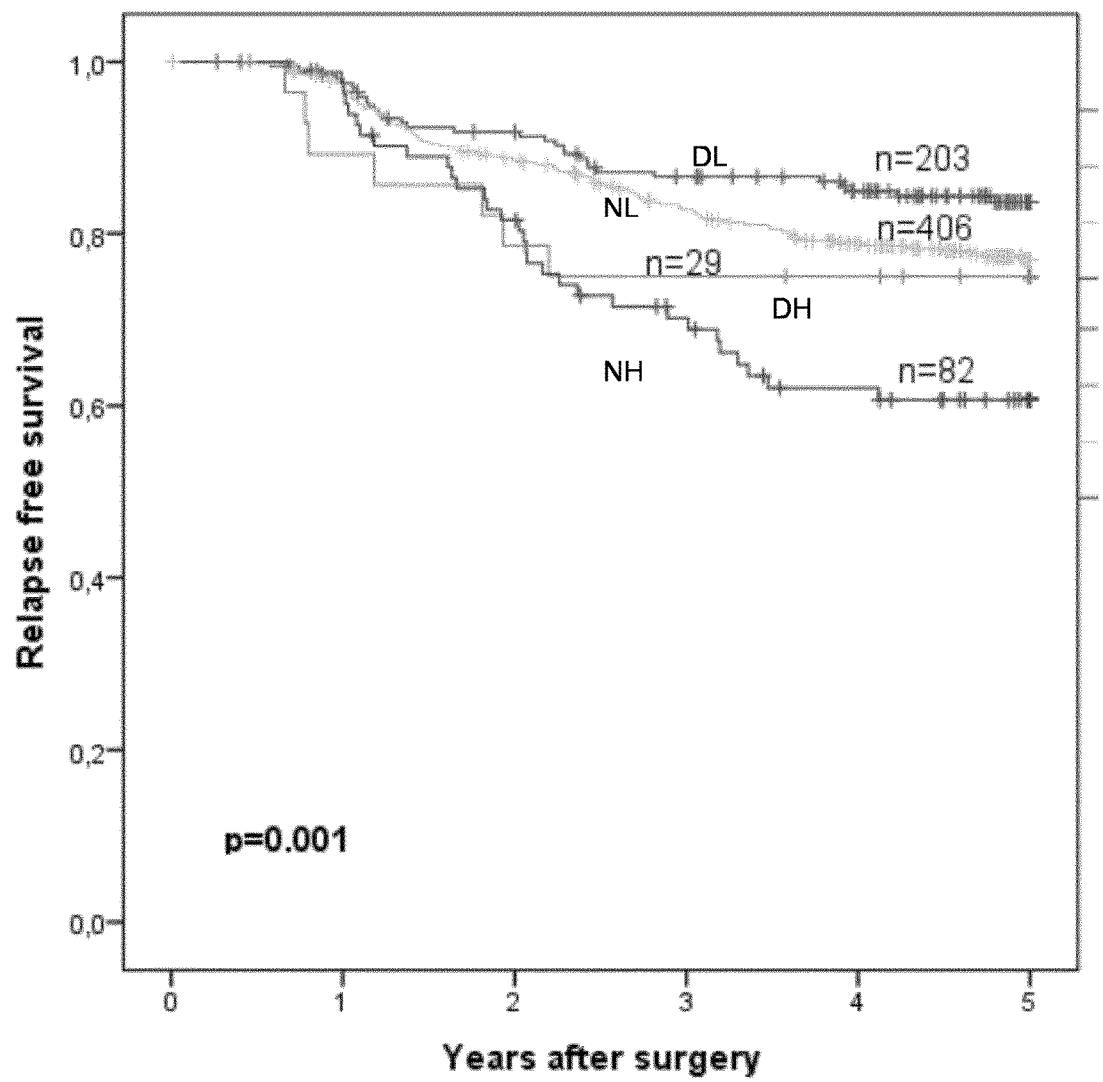
FIG. 10 shows patient survival results in an example using both ploidy and stroma classifications.
Figure 11:
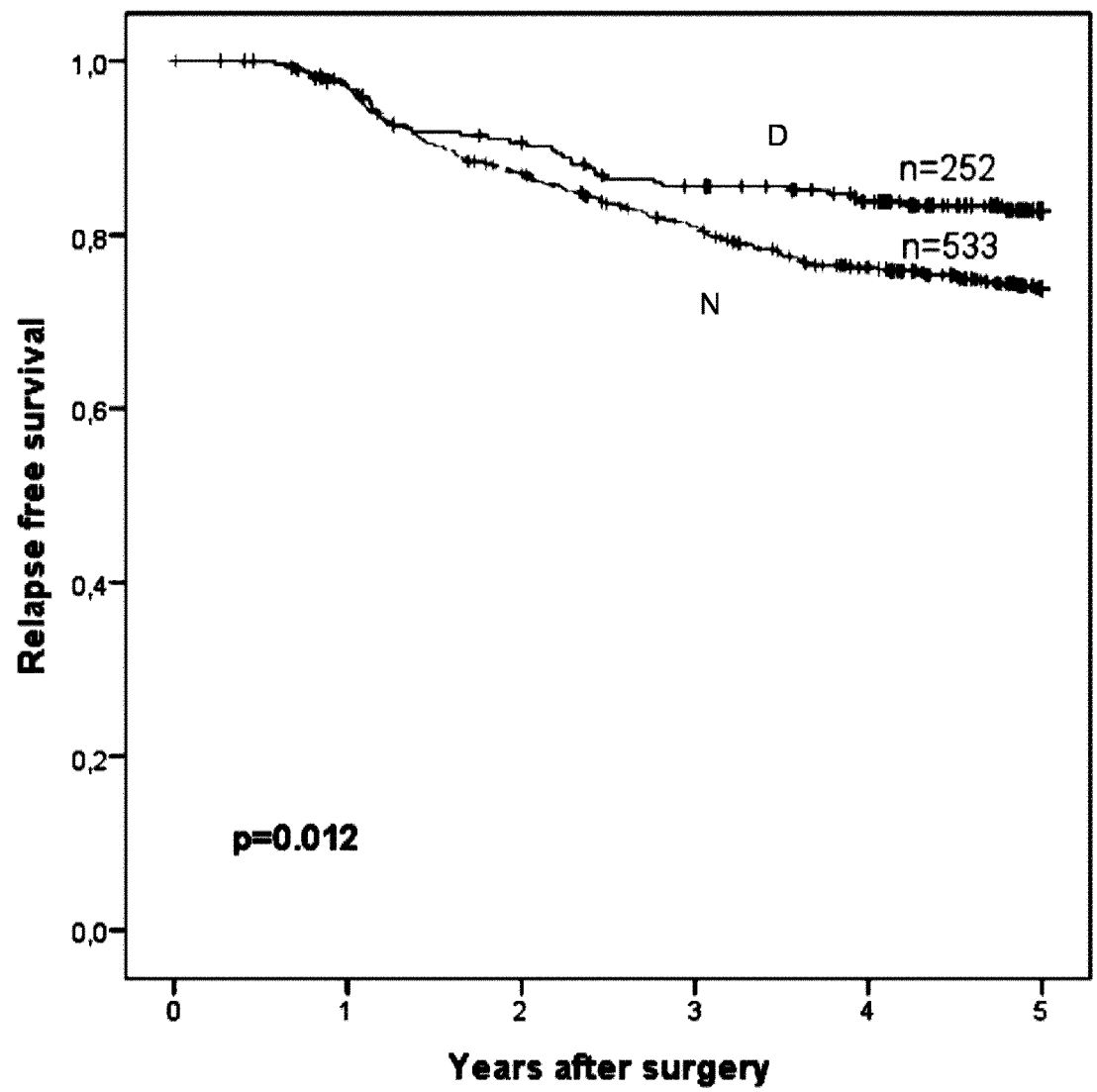
FIG. 11 shows patient survival results in an example using only ploidy classification.

FIG. 10 provides corresponding data for the V series. Again, this graph shows much better separation of life expectancy, and hence diagnostic power, than FIG. 11 which simply shows the results based on classification by ploidy type.

Figure 12:
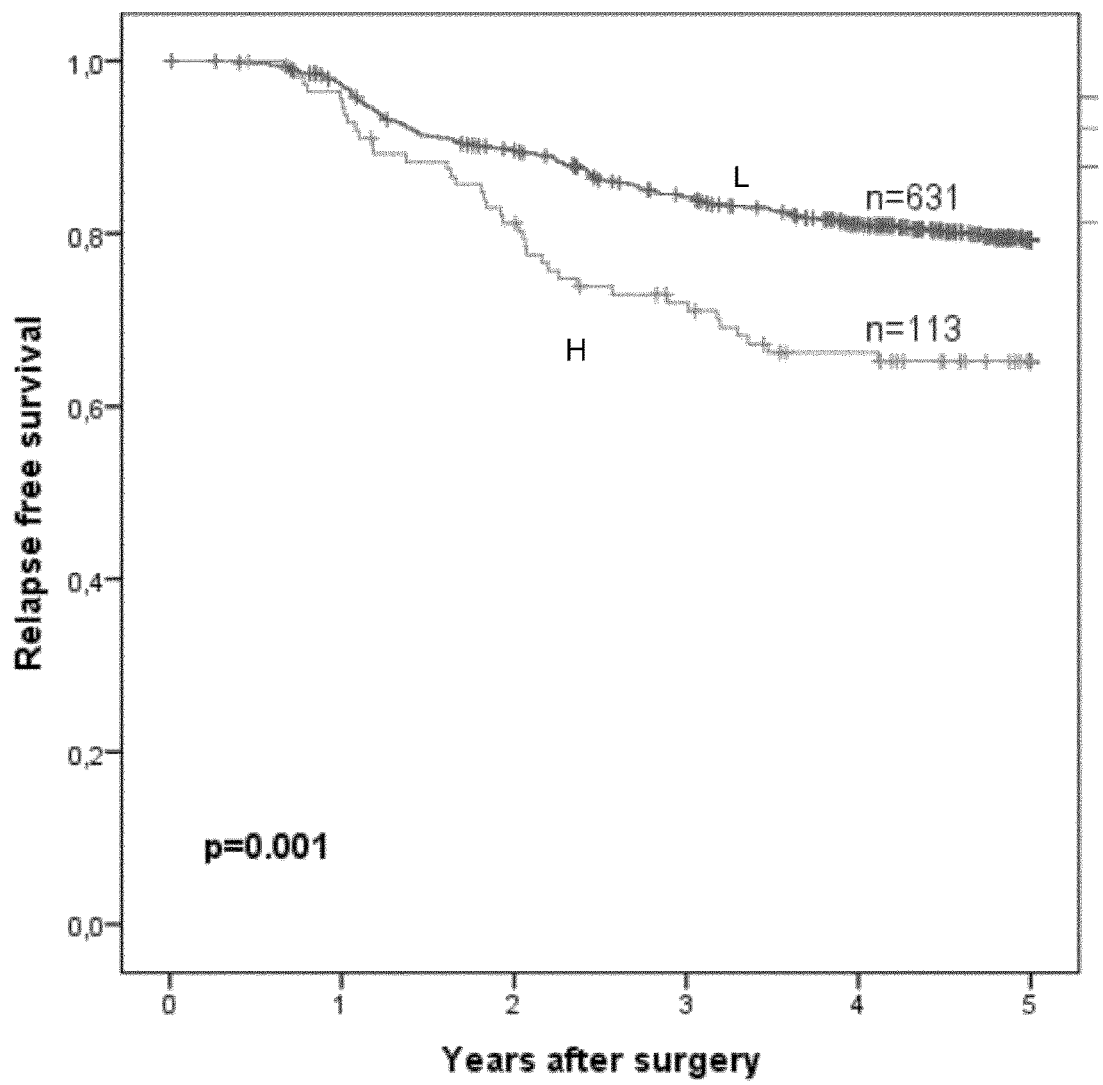
FIG. 12 shows patient survival results in an example using only stroma classification.

FIG. 12 shows the data corresponding to FIG. 10 separated only by stroma type. Note that the results of FIG. 10 are also better than those of FIG. 12 using stroma type alone.

In other words, the combination of stroma and ploidy works better than either alone.

The above results relate to colorectal cancer. However, the same approach works for other types of cancer.

Figure 13:
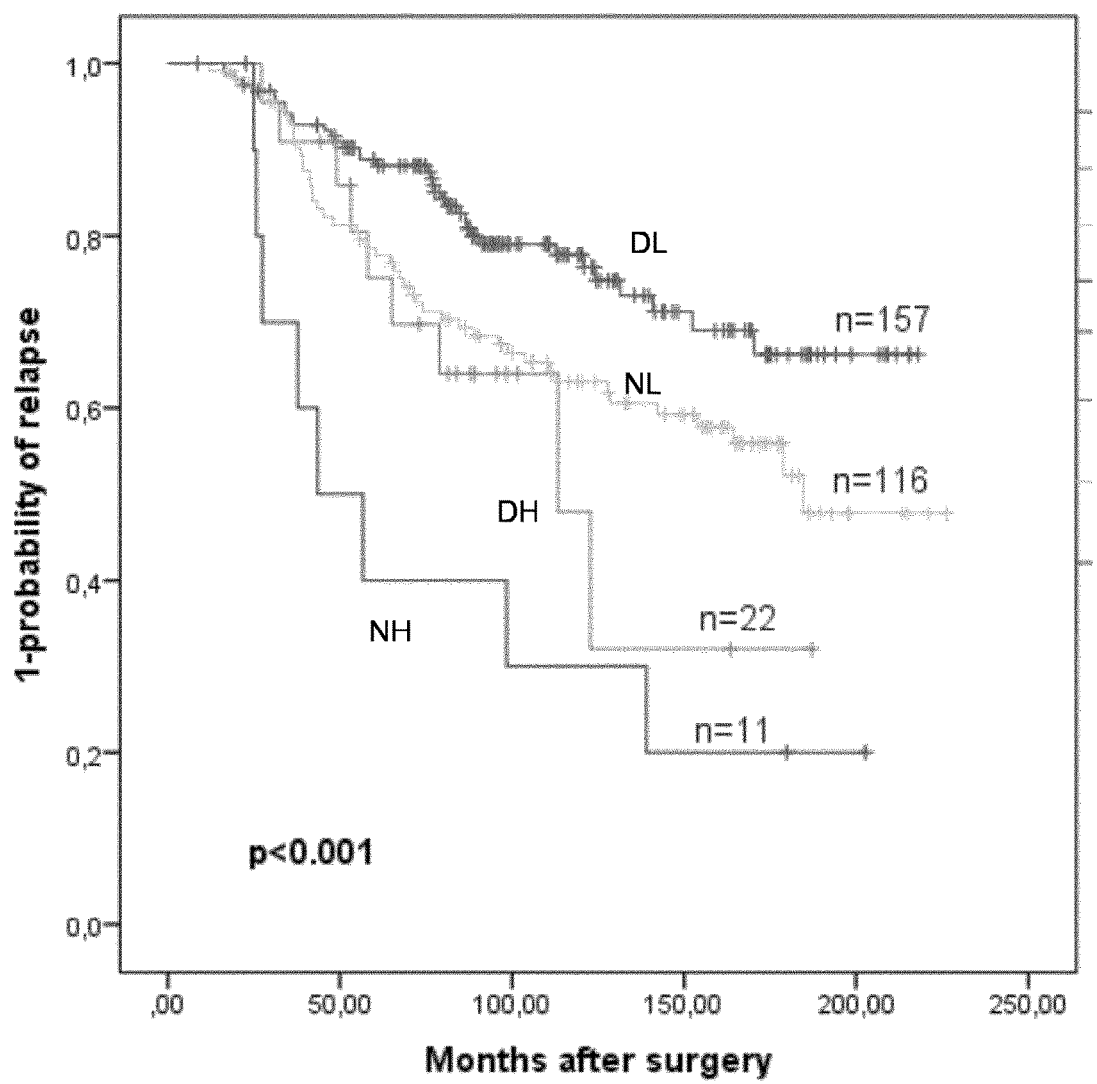
FIG. 13 shows patient survival results in an example using both ploidy and stroma classifications.

FIG. 13 shows the relapse free survival results calculated in the same way for prostate cancer using a classification based both on stroma type and ploidy type.

Figure 14:
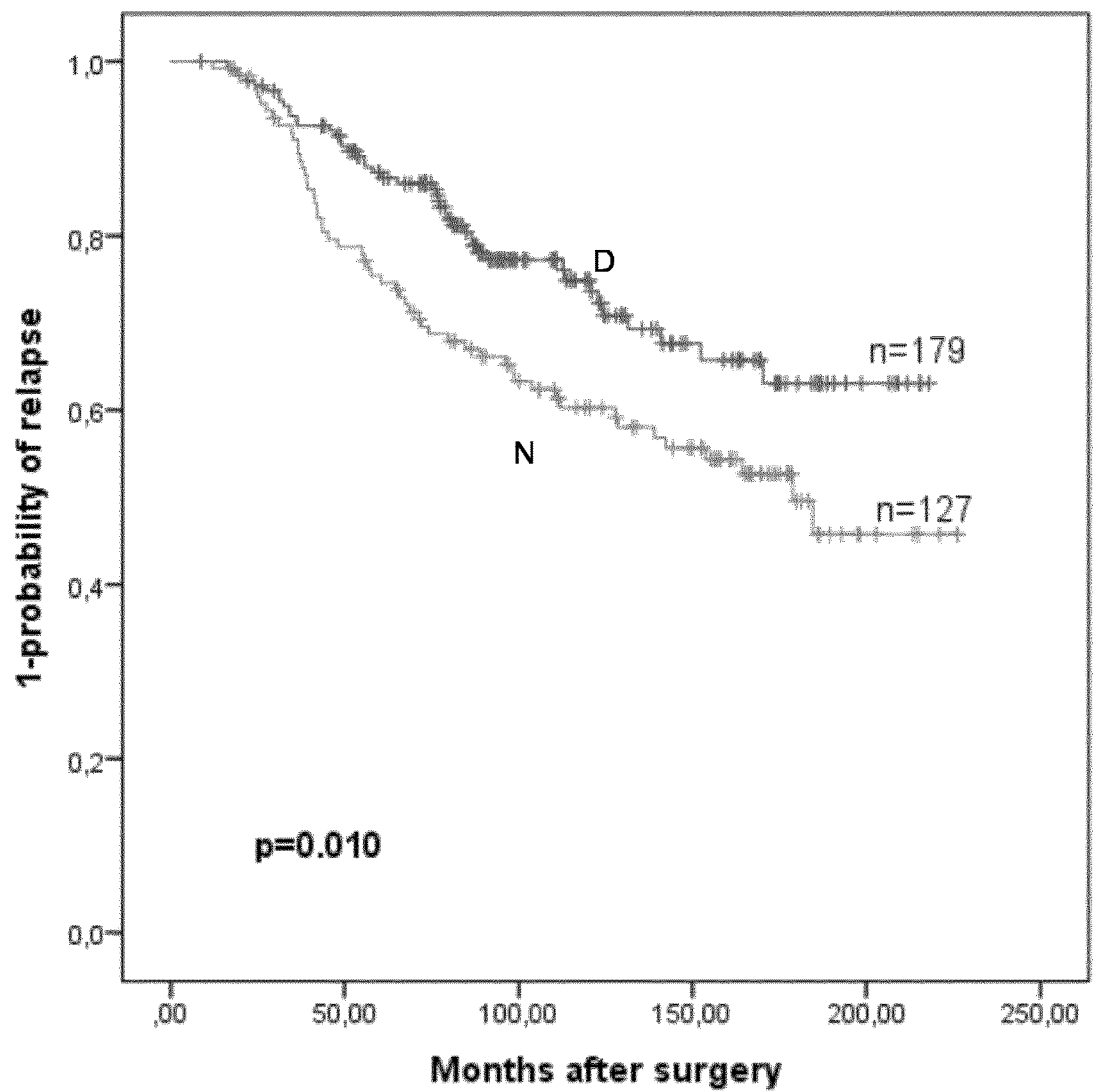
FIG. 14 shows patient survival results in an example using only ploidy classification.

FIG. 14 shows a comparative example using only the ploidy type. Note how much better the results are using the combined approach than only using ploidy.

Thus, the evidence suggests that the method is of general application, not just for colorectal cancer.

Note that in most cases when different measurements are made on the same sample little improvement is obtained in relapse-free survival estimates by combining the estimates instead of simply using the better of the different measurements. However, in this case of the ploidy measurement and stroma measurement described here, the different measurements unexpectedly divide the samples into populations with significantly different outcomes and hence the method gives much better utility in subsequent medical decision-making than using only one of the measurements. In particular, including the stroma measurement significantly improves results compared with measuring ploidy alone.

A further method of identifying stroma will now be described. The method described above uses an image converted into HSV coordinates, automatically extracts two ranges of hue and uses an automatic clustering algorithm on the hue values. Instead, in an alternative arrangement for identifying stroma, both hue and saturation values of the converted image are used. Each is given an equal weighting.

In detail, the method according to the alternative is as follows:

Firstly, a slide of an image stained with a Hematoxylin and Eosin stain is scanned and corrected for white balance using a version of Huo's method as taught in Huo J, et al "Robust Automatic White Balance Algorithm using Gray Color Points in Images", IEEE transactions on Consumer Electronics, 2006, volume 52, number 2, pages 541 to 546.

The image is then extracted and resampled. In an example, the resampling was done with a ratio of 1/8 yielding an image with a linear resolution approximately 2 μm.

The colour channels are then extracted and normalised using the method taught by Macenko M, et al, "A method for normalising histology slides for quantitative analysis", Biomedical Imaging: From Nano to Macro 2009, IEEE international symposium on biomedical imaging ISBI 2009, pages 1107 to 1110. This process in fact results in two images, referred to as the Haematoxylin image and the H and E image. The Haemotoxylin image is a normalised image relating to the Haematoxylin stain not the eosin stain and the H and E image a normalised image corresponding to both hematoxylin and eosin stains.

These images are processed using colour data in the HSV colour space of hue, saturation and value.

Two masks are then created, namely a background mask and a connective tissue mask.

To obtain the background mask, an averaging filter of size 7×7 is applied to the normalized H&E image. Then, pixels with a Value V<0.2 and mean saturation S<0.4 are removed to create the background mask.

To obtain the connective tissue mask, the normalised Haemotoxylin image is gray and median filtered with a 9×9 window to obtain a median image. This image is then processed with a standard deviation filter with a kernel size of 17 to obtain a standard deviation filtered image.

These two images, the median image and the standard deviation filtered image are combined by addition—note that both images are normalised. Histogram adjustment is then performed to adjust the image so that 1% of the low and high values are saturated. The result of this is a combined image.

Using the Otsu's method to calculate a threshold level, the combined image has a threshold applied at 1.15 times this Otsu calculated threshold value. This image is then filtered to remove small objects below 200 pixels in area and a closing filter is applied with a disk kernel of size 3 to obtain a connective tissue mask.

The connective tissue mask and the background mask are then combined using an AND operation to obtain a final mask. The stroma fraction is calculated from the connective tissue fraction (i.e. the stroma) in a region of interest, i.e. the number of pixels of connective tissue (not background) divided by the total number of pixels (not background).

Thus, in this case the method effectively calculates a mask based on two separate masks, one to exclude connective tissue and one to exclude background, improving the method compared with the method above.

To test the results of the method, this method was applied to a number of tumours which were classified—tumours with a stroma fraction less than 50% were classified as low stroma and tumours with a stroma fraction of 50% or higher were classified as high stroma.

Multivariate analysis showed that the method had particular value in stage 3 tumours, and showed that in the sample the relevant prognostic factors were stroma, ploidy and mutation, and T-stage. Accordingly, providing a tool to carry out quantitative analysis using a stroma fraction using the methods taught here as well as ploidy significantly improves diagnostic reliability compared with methods using ploidy but not using stroma fraction.

In particular, for the tested sample, the following multivariate factors were obtained. Hazard ratio is the ratio of the hazard rates described by two conditions, so a hazard ratio of 2 indicates a doubling of risk for the adverse value compared with the positive value. In the results, the metric used was five-year recurrence free survival.

Stroma: Hazard ratio 2.0 (confidence interval 1.4 to 2.9) and p value<0.001

Ploidy: Hazard ratio 1.4 (confidence interval 0.9 to 2.2) and p value 0.14.

T stage: Hazard ratio 1.6 (confidence interval 1.1 to 2.4) and p value b 0.019.

Selecting only stage 3 tumours with T-stage T3 gave even better values:

Stroma: Hazard ratio 2.1 (confidence interval 1.3 to 3.4) and p value 0.003.

Ploidy: Hazard ratio 2.0 (confidence interval 1.1 to 3.3) and p value 0.013. The smaller sample size of course results in greater relative confidence intervals.

Thus, including stroma clearly gives improved results since patients with a high stroma count have double the risk of patients with low stroma.

Although at first sight the method does not involve the hue of the image the method used to separate out the Haemotoxylin image and the H&E image uses hue.

The inventors have found that the method according to this second embodiment gives more reproducible results, i.e. is more robust against changes in image staining and image capture which is of course a significant issue in such image processing. Without wishing to be bound by theory, it is believed that the normalisation that takes place to create the Haemotoxylin image and the H&E image is effective at normalising the images to reduce the effect of such changes in the staining of the sample and in image capture.

Nothing given in the illustrative explanation is intended to limit the scope of the claims.

The invention claimed is:

1. A computer program product stored on a memory device adapted to cause a computer to carry out a method of quantitative analysis of a tissue sample, comprising:
    carrying out a ploidy measurement on a plurality of nuclei of the sample to determine the ploidy type of a sample;
    carrying out a stroma measurement on a section of the tissue sample to determine the stroma type of a sample by determining whether the sample is a high stroma type having a percentage of stroma above a predetermined stroma percentage or a low stroma type having a percentage of stroma at most the predetermined stroma percentage;
    and outputting a classification based on the stroma type and the ploidy type, wherein the stroma measurement is carried out by:
    capturing a microscope image of a stained section from the tissue sample;
    using a clustering algorithm to segment the image pixels of the microscope imaging into stroma and non-stroma pixels; and
    calculating the fraction of stroma pixels in the image; and
    determining whether the fraction of stroma pixels exceeds the predetermined stroma percentage.

2. The computer program product according to claim 1, wherein using a clustering algorithm comprises fitting the image pixels to two Gaussian curves, one Gaussian curve corresponding to stroma and one corresponding to non-stroma regions of the image.

3. The computer program product according to claim 1, further comprising converting the captured microscope image to hue-saturation-value color coordinates before carrying out the step of using a clustering algorithm.

4. The computer program product according to claim 3, wherein the step of using a clustering algorithm includes fitting the hue value of the image pixels to two Gaussian curves, one Gaussian curve corresponding to stroma and one corresponding to non-stroma regions of the image.

5. The computer program product according to claim 2, wherein the captured image has a Haemotoxylin and eosin stain, further comprising:
    converting the captured image into a normalized Haemotoxylin image representing the areas of the image stained with Haemotoxlyin and a normalized Haemotoxylin and eosin image representing the areas of the image stained with either Haemotoxylin or eosin;
    calculating a background mask of pixels in the normalized Haemotoxylin and eosin image having saturation below a first predetermined level and value below a second predetermined level corresponding to the background of the image; and
    calculating a connective tissue mask by converting the normalized Haemotoxyin image to gray to obtain a gray-converted image;
    wherein the step of using a clustering algorithm uses a clustering algorithm and thresholding on the gray converted image to identify pixels of connective tissue.

6. The computer program product according to claim 1, wherein the predetermined stroma percentage is 30% to 70%.

7. The computer program product according to claim 1, wherein the ploidy measurement is carried out by:
    capturing a microscope image of a nuclei specimen, prepared from a sample of tissue such that the nuclei are liberated and stained with a DNA specific stain;
    segmenting the image in the captured image to identify the nuclei;
    for each of a plurality of nuclei, obtaining the integrated optical density; and
    determining the DNA ploidy classification for the sample.

8. The computer program product according to claim 1, further comprising:
    calculating a relapse-free survival group from the stroma type and the ploidy type.

9. The computer program product according to claim 1, wherein a sample of stroma type high stroma and a ploidy type of non-diploid is classified as high risk, a sample of stroma type low stroma and ploidy type diploid indicates a low risk, and wherein samples having a stroma type of low stroma and a ploidy type of non-diploid type or a stroma type of high stroma and a ploidy type of diploid indicate intermediate levels of risk.

10. The computer program product according to claim 1, wherein the tissue sample is from cancerous tissue.

11. The computer program product according to claim 10, wherein the cancerous tissue is prostate tissue, colon tissue or rectal tissue.

* * * * *